(12) United States Patent
Bensimon et al.

(10) Patent No.: US 9,512,476 B2
(45) Date of Patent: Dec. 6, 2016

(54) METHOD OF DNA SEQUENCING BY HYBRIDISATION

(75) Inventors: David Bensimon, Paris (FR); Jean-François Allemand, Arcueil (FR); Maria Manosas, Barcelona (ES); Fang-Yuan Ding, Alhambra, CA (US); Vincent Croquette, Antony (FR)

(73) Assignees: CENTRE NATIONAL DE LA RECHERCHE SCIENTIFIQUE (CNRS), Paris (FR); ECOLE NORMALE SUPERIEURE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 143 days.

(21) Appl. No.: 13/700,109

(22) PCT Filed: May 26, 2011

(86) PCT No.: PCT/EP2011/058669
§ 371 (c)(1),
(2), (4) Date: Feb. 11, 2013

(87) PCT Pub. No.: WO2011/147931
PCT Pub. Date: Dec. 1, 2011

(65) Prior Publication Data
US 2013/0137098 A1 May 30, 2013

Related U.S. Application Data

(60) Provisional application No. 61/377,621, filed on Aug. 27, 2010.

(30) Foreign Application Priority Data

May 27, 2010 (EP) .................................... 10305564

(51) Int. Cl.
C12Q 1/68 (2006.01)
C12P 19/34 (2006.01)
C07H 21/02 (2006.01)
C07H 21/04 (2006.01)

(52) U.S. Cl.
CPC ........... *C12Q 1/6869* (2013.01); *C12Q 1/6874* (2013.01)

(58) Field of Classification Search
USPC ......... 435/6.1, 6.11, 6.12, 91.1, 91.2, 91.51; 436/94, 501; 536/23.1, 24.3, 24.33, 536/25.3
See application file for complete search history.

(56) References Cited

U.S. PATENT DOCUMENTS

| | | | |
|---|---|---|---|
| 4,849,077 A | 7/1989 | Rosenthal et al. | |
| 4,882,127 A | 11/1989 | Rosenthal et al. | |
| 6,723,513 B2 | 4/2004 | Lexow | |
| 7,556,922 B2 | 7/2009 | Block et al. | |
| 2003/0027187 A1 | 2/2003 | Strick et al. | |
| 2003/0166232 A1 | 9/2003 | Saras et al. | |
| 2003/0166262 A1 | 9/2003 | Strick et al. | |
| 2006/0275782 A1 | 12/2006 | Gunderson et al. | |
| 2008/0020392 A1 | 1/2008 | Block et al. | |
| 2009/0181385 A1 | 7/2009 | McKernan et al. | |
| 2009/0181860 A1 | 7/2009 | McKernan et al. | |
| 2009/0186349 A1 | 7/2009 | Gunderson et al. | |

FOREIGN PATENT DOCUMENTS

| | | |
|---|---|---|
| EP | 1141399 B1 | 8/2005 |
| WO | 03066896 A2 | 8/2003 |
| WO | 2006084132 A2 | 8/2006 |
| WO | 2007111924 A2 | 10/2007 |
| WO | 2010016937 A2 | 2/2010 |

OTHER PUBLICATIONS

Ding et al., Single-molecule mechanical identification and sequencing. Nature Method, 9, 367-372, 2012.*
International Search Report for PCT/EP2011/058669 Mailed Jul. 20, 2011.
Cloonan et al., Nat. Methods. 2008;5(7):613-619.
Fuller et al., Nature Biotechnol. 2009;27(11):1013-1023.
Hutchinson, Nucl. Acids Res. 2007;35(18):6227-6237.
Maier et al., Proc Natl Acad Sci U.S.A. 2000;97(22):12002-12007.
Walter et al., Proc Natl Acad Sci U.S.A., 2009;106(31):12950-12955.
Shendure et al., Nature Biotechnol. 2008;26(10):1135-1145.
Ding et al. "Single-Molecule Mechanical Identification and Sequencing: Proof of Principle." Nat Methods, 2012, vol. 9, No. 5, 367-372.
Manosas et al., "Mechanism of strand displacement synthesis by DNA replicative polymerases." Nucleic Acids Research, 2012, vol. 40, No. 13, 6174-6186.

* cited by examiner

*Primary Examiner* — Frank Lu
(74) *Attorney, Agent, or Firm* — Law Office of Salvatore Arrigo and Scott Lee, LLP

(57) ABSTRACT

Described herein is a method for determining a nucleic acid sequence, said method comprising: a) denaturing a double-stranded nucleic acid molecule corresponding to the said nucleic acid sequence by applying a physical force to the said molecule; b) providing a single-stranded nucleic acid molecule; c) renaturing the said double stranded nucleic acid molecule in the presence of the said single-stranded nucleic acid molecule; and d) detecting a blockage of the renaturation of the double-stranded nucleic acid.

18 Claims, 8 Drawing Sheets

```
                         SEQUENCE LISTING

<160> NUMBER OF SEQ ID NOS: 14

<210> SEQ ID NO 1
<211> LENGTH: 12
<212> TYPE: DNA
<213> ORGANISM: Artificial Sequence
<220> FEATURE:
<223> OTHER INFORMATION: Probe

<400> SEQUENCE: 1
acagccagcc ga                                                           12

<210> SEQ ID NO 2
<211> LENGTH: 11
<212> TYPE: DNA
<213> ORGANISM: Artificial Sequence
<220> FEATURE:
<223> OTHER INFORMATION: Probe

<400> SEQUENCE: 2
acagccagcc g                                                            11

<210> SEQ ID NO 3
<211> LENGTH: 10
<212> TYPE: DNA
<213> ORGANISM: Artificial Sequence
<220> FEATURE:
<223> OTHER INFORMATION: Probe

<400> SEQUENCE: 3
acagccagcc                                                              10

<210> SEQ ID NO 4
<211> LENGTH: 9
<212> TYPE: DNA
<213> ORGANISM: Artificial Sequence
<220> FEATURE:
<223> OTHER INFORMATION: Probe

<400> SEQUENCE: 4 acagccagc                                                                9

<210> SEQ ID NO 5
<211> LENGTH: 12
<212> TYPE: DNA
<213> ORGANISM: Artificial Sequence
<220> FEATURE:
<223> OTHER INFORMATION: Target

<400> SEQUENCE: 5
tcggctggct gt                                                           12
```

-continued

```
<210> SEQ ID NO 6
<211> LENGTH: 12
<212> TYPE: DNA
<213> ORGANISM: Artificial Sequence
<220> FEATURE:
<223> OTHER INFORMATION: Probe

<400> SEQUENCE: 6
agccgaccga ca                                                         12

<210> SEQ ID NO 7
<211> LENGTH: 12
<212> TYPE: DNA
<213> ORGANISM: Artificial Sequence
<220> FEATURE:
<223> OTHER INFORMATION: Probe

<400> SEQUENCE: 7
agccgaccga ct                                                         12

<210> SEQ ID NO 8
<211> LENGTH: 12
<212> TYPE: DNA
<213> ORGANISM: Artificial Sequence
<220> FEATURE:
<223> OTHER INFORMATION: Probe

<400> SEQUENCE: 8
agccgaccgt ca                                                         12

<210> SEQ ID NO 9
<211> LENGTH: 12
<212> TYPE: DNA
<213> ORGANISM: Artificial Sequence
<220> FEATURE:
<223> OTHER INFORMATION: Probe

<400> SEQUENCE: 9
agccgtccga ca                                                         12

<210> SEQ ID NO 10
<211> LENGTH: 12
<212> TYPE: DNA
<213> ORGANISM: Artificial Sequence
<220> FEATURE:
<223> OTHER INFORMATION: Probe

<400> SEQUENCE: 10
agccgtgcga ca                                                         12

<210> SEQ ID NO 11
<211> LENGTH: 12
<212> TYPE: DNA
<213> ORGANISM: Artificial Sequence
<220> FEATURE:
<223> OTHER INFORMATION: Probe

<400> SEQUENCE: 11
agccgtccca ca                                                         12

<210> SEQ ID NO 12
<211> LENGTH: 10
<212> TYPE: DNA
<213> ORGANISM: Artificial Sequence
<220> FEATURE:
<223> OTHER INFORMATION: Probe
```

```
<400> SEQUENCE: 12
acagccagcc                                                                  10

<210> SEQ ID NO 13
<211> LENGTH: 128
<212> TYPE: DNA
<213> ORGANISM: Artificial Sequence
<220> FEATURE:
<223> OTHER INFORMATION: Probe

<400> SEQUENCE: 13
gcacgcactc gctcgcgcca gccagccagc catcgctcgc gcacgcacgc acgcacccga           60
ccgaccgacc gagccagcca gcacgcacgc cagccaccga ccgatcgctc gctcgctcgc          120
ccgaccga                                                                  128

<210> SEQ ID NO 14
<211> LENGTH: 16
<212> TYPE: DNA
<213> ORGANISM: Artificial Sequence
<220> FEATURE:
<223> OTHER INFORMATION: Probe

<400> SEQUENCE: 14
gcttcggaat gtacca                                                          16
```

METHOD OF DNA SEQUENCING BY HYBRIDISATION

CROSS REFERENCE TO RELATED APPLICATIONS

This application is a §371 National Stage Application PCT/EP2011/058669 filed May 26, 2011, which claims priority to European Application No. 10305564.6 filed May 27, 2010 and U.S. Application No. 61/377,621, filed Aug. 27, 2010.

BACKGROUND OF THE INVENTION

1. Field of the Invention

The present invention relates to a fast method for the determination of a sequence of a nucleic acid, DNA or RNA, which is useful, in particular, for the sequencing of an unknown nucleic acid or alternatively for the detection of a specific nucleic acid sequence for diagnosis.

2. Description of Related Art

Nowadays, the determination of nucleic acid sequence is at the heart of molecular biology. For example, a broad range of biological phenomena can be assessed by high-throughput DNA sequencing, e.g., genetic variation, RNA expression, protein-DNA interactions and chromosome conformation (see, for a few examples, Mitreva & Mardis, *Methods Mol. Biol.*, 533:153-87, 2009; Mardis, *Genome Med.*, 1(4): 40, 2009; Cloonan et al., *Nat Methods*, 5(7): 613-619, 2008; Valouev et al., *Genome Res.*, 18(7):1051-63, 2008, Valouev et al., *Nat. Methods.*, 5(9):829-34, 2008; Orscheln et al., *Clin Infect Dis.*, 49(4):536-42, 2009; Walter et al., *Proc Natl Acad Sci USA.*, 106(31):12950-5, 2009; Mardis et al., *N Engl J. Med.*, 361(11):1058-66, 2009, Hutchinson, *Nucl. Acids Res.*, 35(18): 6227-6237, 2007).

In addition, demonstration of the presence of a specific DNA sequence in a physiological sample constitutes, at the present time, the major line of development of diagnostic methods, e.g. for identifying the probability of bacteria of developing antibiotic resistance, genetic abnormalities, the risks of cancer associated with genetic modifications and viral infections, for example infections associated with HIV or with hepatitis viruses (see for example Zhang et al., *Nature*, 358: 591-593, 1992; Turner et al., *J Bacteriol*, 176(12):3708-3722, 1994; Weston et al., *Infection and Immunity.*, 77(7):2840-2848, 2009).

Nucleic acid sequencing is nowadays carried out chiefly with capillary-based, semi-automated implementations of the Sanger biochemistry. The classical method comprises a step of amplification of the DNA of interest, followed by a step of 'cycle sequencing', wherein each round of primer extension is stochastically terminated by the incorporation of fluorescently labelled dideoxynucleotides (ddNTPs). Sequence is determined by high-resolution electrophoretic separation of the single-stranded, end-labelled extension products in a capillary based polymer gel. Simultaneous electrophoresis in 96 or 384 independent capillaries provides a limited level of parallelization.

The high demand for low-cost sequencing has driven the development of high-throughput sequencing technologies that parallelize the sequencing process, producing thousands or millions of sequences at once (Shendure & Ji, *Nat. Biotechnol.*, 26(10):1135-45. 2008). High-throughput sequencing technologies are intended to lower the cost of DNA sequencing beyond what is possible with standard dye-terminator methods. At present this very high throughput is achieved with substantial sacrifices in length and accuracy of the individual reads when compared to Sanger sequencing. Examples of such new methods include the 454 and the Solexa technologies. These technologies allow shotgun sequencing of whole genomes without cloning in *E. coli* or any host cell. Libraries of short, adaptor-flanked DNA fragments captured on the surface of beads are amplified by emulsion PCR. Sequencing is carried out using primed synthesis by DNA polymerase. In the 454 method (also known as 'pyrosequencing'), the array is presented with each of the four dNTPs, sequentially, and the amount of incorporation is monitored by luminometric detection of the pyrophosphate released. A key difference between this method and the Solexa is that the latter uses chain-terminating nucleotides. The fluorescent label on the terminating base can be removed to leave an unblocked 3' terminus, making chain termination a reversible process. The SOLiD technology relies on the ligation of fluorescently labeled di-base probes to a sequencing primer hybridized to an adaptor sequence within the clonally-amplified library template. Specificity of the di-base probe is achieved by interrogating every 1st and 2nd base in each ligation reaction. Multiple cycles of ligation, detection and cleavage are performed with the number of cycles determining the eventual read length. In contrast to the three previous technologies, which all require a first step of amplification, the Helicos platform allows the sequencing of single DNA molecules. This technology is based on the use of a highly sensitive detection system of fluorescent nucleotides incorporation to directly interrogate single DNA molecules via sequencing by synthesis.

Such methods are described in e.g. U.S. Pat. No. 4,882,127, U.S. Pat. No. 4,849,077; U.S. Pat. No. 7,556,922; U.S. Pat. No. 6,723,513; PCT Patent Application No. WO 03/066896; PCT Patent Application No. WO2007111924; U.S. Patent Application No. US 2008/0020392; PCT Patent Application No. WO 2006/084132; U.S. Patent Application No. US 2009/0186349; U.S. Patent Application No. US 2009/0181860; U.S. Patent Application No. US 2009/0181385; U.S. Patent Application No. US 2006/0275782; European Patent EP-B1-1141399; Shendure & Ji, *Nat. Biotechnol.*, 26(10):1135-45. 2008; Pihlak et al., *Nat. Biotechnol.*, 26(6): 676-684, 2008; Fuller et al., *Nature Biotechnol.*, 27(11): 1013-1023, 2009; Mardis, *Genome Med.*, 1(4): 40, 2009; Metzker, *Nature Rev. Genet.*, 11(1): 31-46, 2010.

However, all the methods developed so far suffer from serious drawbacks. In particular, they all make use of labelled nucleotides (e.g. fluorescent), thus contributing to seriously increasing the overall costs. Moreover, all these new methods bar one (the Helicos platform) require amplification of the target sequence prior to sequencing, which is time consuming on the one hand, increases the probability of errors on the other hand, and is highly prone to contamination.

SUMMARY

The method according to the present invention, based on physical techniques and electronic treatments, differs from the current approaches, which are chemical or biochemical. Its advantages are numerous:

1) It allows the sequencing of a single molecule, and thus does not require a previous amplification step (e.g. by PCR).
2) It is far cheaper than the methods of the art since standard single-stranded nucleic acid molecules are used, which are far less expensive than labelled nucleotides (either with fluorophores or some other groups).

Moreover the quantity of the standard single-stranded nucleic acid molecules is reduced to a minimum since the sequence of a single double-stranded nucleic acid molecule is determined. In addition, in some embodiments at least, the probing strands could be reused as they are not consumed in the sequencing process.

3) It enables to determine the localization (in bp) of a paired single-stranded nucleic acid molecule along a double-stranded nucleic acid by measuring the distance between the two ends of the said double-stranded nucleic acid molecule.
4) It permits to determine in one renaturation assay the different hybridization positions of an oligonucleotide on a given double-stranded nucleic acid hairpin.
5) The measurement can be repeated periodically on a second time-scale, thus leading to elimination of false positives (spurious partial hybridizations), improved statistics and allowing for a significant reduction in instrumental drifts.
6) The experiment can be repeated many times on the same molecule, thus improving the statistics and the reliability of the measurement, since the hybridized single stranded nucleic acid can be ejected (by e.g. reducing the force or the ionic strength or by using a helicase or a nuclease) during the completion of the renaturation phase.
7) It allows for the parallel sequencing of various double-stranded nucleic acid molecules, since each molecule can be manipulated independently of the others.

The present invention relates to a method for the determination of a nucleic acid sequence, wherein the renaturation of a denatured double stranded nucleic acid corresponding to the said nucleic acid sequence is blocked.

DETAILED DESCRIPTION OF A PREFERRED EMBODIMENT

Figure 1:
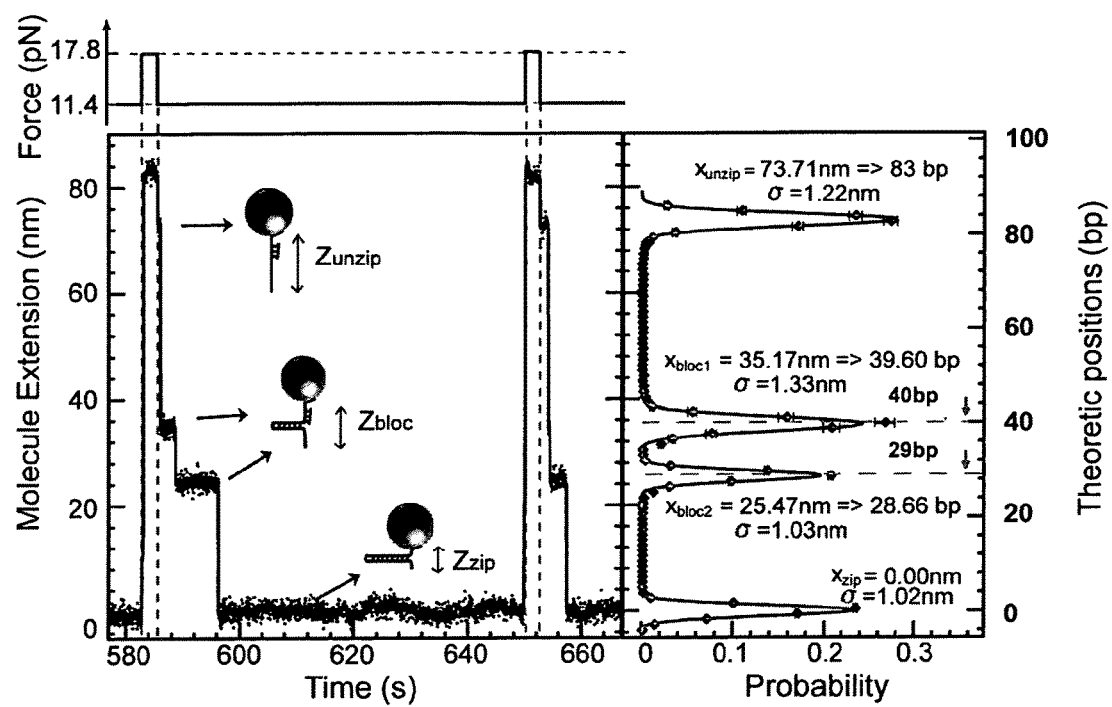
FIGS. 1, 2A-2C, 3, 4, 5a, 5b, 6 and 7 represent embodiments as described herein.

By 'determination of a nucleic acid sequence', it is herein meant not only the deciphering of the actual succession of bases in a nucleic acid, but also all the activities leading directly or indirectly to the obtention of some information on nucleic acid sequence, such as the detection of a particular sequence in a nucleic acid molecule or the detection of a difference between the sequences of two different nucleic acid molecules.

The invention is based on the observation that the two strands of a denatured double-stranded nucleic acid will rehybridize under appropriate conditions. If some molecules are bound to any of the strands of the said denatured double-stranded nucleic acid during the renaturation step, the rehybridization will only be partial. The inventors have now found that, under certain conditions, this pause in rehybridization, permanent or transient, can be used to obtain information about the sequence contained in the denatured double-stranded nucleic acid molecule. According to the invention, it is possible to detect a blockage of the rehybridization of the double-stranded nucleic acid molecule; the physical parameters (e.g. the duration of the blockage, the position of the blockage on the double-stranded nucleic acid molecule) associated with this blockage then allow the determination of the sequence of the nucleic acid.

The present invention thus relates to a method for the determination of a nucleic acid sequence, said method comprising a step of detecting a blockage of the renaturation of a denatured double stranded nucleic acid corresponding to the said nucleic acid sequence. By 'denaturation', it is herein meant the process of strands separation of a double-stranded nucleic acid molecule occurring when most of the hydrogen bonds between the said strands are broken. The denaturation process yields a denatured nucleic acid molecule, by which it is herein meant the two separated complementary strands resulting from the denaturation of a double-stranded nucleic acid molecule. By 'renaturation', it is herein referred to the process by which two separated complementary strands reform through hybridization into a double helix. As used herein, 'hybridization' is the process of establishing a non-covalent, sequence-specific interaction between two or more complementary strands of nucleic acids into a single hybrid.

There are several possibilities known to the skilled person to denature the nucleic acid. In a most preferred manner, the two strands are separated by submitting them to a physical force. For example, the free ends of the said double-stranded nucleic acid may be pulled apart, thus rupturing all the bonds between the paired bases, and opening the double-stranded nucleic acid.

Thus, in one embodiment, the method of the invention relates to a method for the determination of a nucleic acid sequence, said method comprising the steps of:
denaturing a double-stranded nucleic acid molecule corresponding to the said nucleic acid sequence by applying a physical force to the said molecule; and
detecting a blockage of the renaturation of the double-stranded nucleic acid.

In this type of sequence determination method, it can be advantageous, in order to facilitate re-pairing, to arrange for the free ends of the double-stranded DNA (i.e. the ends which are not attached to supports) to be joined to one another covalently or quasi-covalently before pulling apart. In a preferred embodiment, the double-stranded nucleic acid molecule is a hairpin. If it is desired that the double-stranded nucleic acid be represented diagrammatically in the context of the present invention, it is possible to liken it to a "zip fastener", which is opened (or closed): the denaturation of the double-stranded nucleic acid is the unzipping, the renaturation the rezipping.

The inventors have observed that, under certain conditions, when a molecule is bound to the denatured double-stranded nucleic acid molecule, renaturation of the said molecule is blocked. The molecule bound can be of any type of molecule with an affinity for a specific sequence on the said denatured double-stranded nucleic acid molecule, e.g. a nucleic acid, a protein or a small molecule. However, it is preferable to use a single-stranded nucleic acid, since the said single-stranded nucleic acid can hybridize with a complementary sequence on one of the strands of the denatured double-stranded nucleic acid. This single-stranded nucleic acid can be of any length, provided that it is long enough to block the renaturation process. Preferentially, the length of the single stranded nucleic acid will be comprised between 3 and 20 nucleotides, more preferentially, between 7 and 15 and even more preferentially between 8 and 12.

The single-stranded nucleic acid of the invention can be in particular a DNA or an RNA molecule, either natural or modified. The said single-stranded nucleic acid may also be made of modified nucleotides, such as locked nucleic acid (LNA), which are nucleotides in which the ribose moiety is modified with an extra bridge connecting the 2' oxygen and 4' carbon, or peptide nucleic acid (PNA), wherein the backbone is composed of repeating N-(2-aminoethyl)-glycine units linked by peptide bonds.

When a single-stranded nucleic acid molecule is added to a denatured double-stranded nucleic acid prior to renaturation, a blockage of rehybridization indicates that the sequence of the single-stranded nucleic acid molecule is complementary to at least part of the sequence of the double-stranded nucleic acid molecule.

Thus, the method of the invention also relates to a method for the determination of a nucleic acid sequence, said method comprising the steps of:
a) denaturing a double-stranded nucleic acid molecule corresponding to the said nucleic acid sequence by applying a physical force to the said molecule;
b) providing a single-stranded nucleic acid molecule;
c) renaturing the said double stranded nucleic acid molecule in the presence of the said single-stranded nucleic acid molecule; and
d) detecting a blockage of the renaturation of the double-stranded nucleic acid.

The invention applies to any type of double-stranded nucleic acid. Most often, the double-stranded nucleic acid will be DNA, but it is understood that the invention also applies to single-stranded DNA-single-stranded DNA duplexes, perfectly paired or not perfectly paired, or alternatively to single-stranded DNA-single-stranded RNA duplexes, perfectly paired or not perfectly paired, or alternatively to single-stranded RNA-single-stranded RNA duplexes, perfectly paired or not perfectly paired. Furthermore, the duplex may consist of the at least partial re-pairing of two single strands obtained from samples of different origins. Finally, the invention also applies to the secondary structures of a sole single-stranded DNA or of a sole single-stranded RNA.

In a typical configuration, the double-stranded nucleic acid molecules may be specifically anchored on two solid substrates (e.g. microscope slide, micropipette, microparticle). One of the ends may be attached directly or indirectly to a surface, while the other end is attached directly or indirectly to a movable surface. In this embodiment, a tension is applied on both ends of the double-stranded nucleic acid when the supports are moved away. When the tension is higher than a threshold value, the two strands are separated and the nucleic acid molecule is denatured. The tension applied is preferentially above or equal to 15 pN; it is more preferentially above or equal to 16 pN; it is even more preferentially above or equal to 17 pN; in a very much preferred aspect, it is above or equal to 18 pN. This force may vary with temperature, nucleotide type and buffer, but the skilled person will easily adapt the said force with regard to these parameters in order to obtain the separation of the two strands. On the other hand, when the tension is decreased under a minimal value, the two strands of the denatured double-stranded nucleic acid can rehybridize. To obtain rehybridization of the said two strands, a tension of less than or equal to 12 pN is preferentially applied; more preferentially, it is less than or equal to 11 pN; even more preferentially, it is less than or equal to 10 pN. Most preferably, the double-stranded nucleic acid is a hairpin. As used herein, 'hairpin' means a double helix wherein the 5' end of one strand is physically linked to the 3' end of the other strand through an unpaired loop. The said physical link can be either covalent or non covalent. Preferentially, the said physical link is a covalent bond. Thus, a hairpin consists of a double-stranded stem and an unpaired single-stranded loop. In a hairpin, the ends of the two strands which are not engaged in the loop are free and can thus be pulled apart. This results in the unpairing of the double stranded nucleic acid, thus yielding a denatured double stranded nucleic acid molecule. It is possible to open completely a hairpin double-stranded nucleic acid molecule by pulling on each end of the said nucleic acid molecule with a force higher than a threshold value. When the tension applied to the molecule is decreased to less than a minimal value, the nucleic acid molecule rehybridizes to reform a hairpin. The presence of a single-stranded nucleic acid molecule hybridized to one of the nucleic acid strand leads to a pause in rehybridization. Therefore, the detection of such a pause indicates that the single-stranded nucleic acid molecule comprises a sequence which is complementary to at least part of the double-stranded stem.

It is advantageous in this respect to design the loop sequence and length so that the hairpin refolds after a short transient, e.g. 1 s. Methods to this effect have been described in the prior art, e.g. in Woodside et al., *Proc. Natl. Acad. Sci. U.S.A.*, 103 (16): 6190-6195, 2006). When the force is decreased from the opening to the test value, the extension of the open hairpin varies because of the elasticity of single stranded DNA. The small delay before the hairpin refolds allows the user to determine the hairpin extension at the same force than the one used to detect the blocking state.

Using a hairpin makes it possible, in particular, to perform cycles of pairing and unpairing and thus to improve the signal/noise ratio.

Techniques allowing the free ends of double-stranded nucleic acid to be joined together are known, and some will be described in greater details in what follows.

By determination of the blockage, it is herein meant the determination of the physical parameters associated with the blockage. The most useful of these parameters is the position of the blockage on the double-stranded nucleic acid molecule, said position corresponding to the position of hybridization of the single-stranded nucleic acid molecule on the double-stranded nucleic acid molecule. Indeed, the inventors have found that the position on the double-stranded nucleic acid at which the pause in renaturation occurs can be precisely determined: the use of a hairpin affords the skilled person a means to determine the physical distance between the two free ends of the hairpin at any time during the denaturation/renaturation process.

By 'free end' it is herein meant the end of one strand which is not covalently linked to an extremity of the other strand; as explained above, these free ends may each be bound to a different surface. For example, one of these surfaces may be movable, whilst the other may be motionless. The skilled person will thus easily realize that, in order to measure the distance between the free ends of the hairpin double-stranded nucleic acid, it is possible to simply measure the distance between the two surfaces.

This distance is maximal ($z_{high}$ ($F_{open}$)) when the hairpin molecule is completely denatured, since the hairpin nucleic acid is then completely extended; it is minimal ($z_{low}$ ($F_{test}$)) when the said hairpin molecule is completely renatured. It is advantageous to perform all length comparisons at the same force $F_{test}$, so that the single stranded nucleic acid has the same elastic properties. Using the delay in loop closing the skilled user can measure $z_{high}$ ($F_{test}$). Likewise, the distance between the two free ends when the renaturation process is temporarily paused can be measured: as expected, this distance z is comprised between $z_{high}$ and $z_{low}$ (all z being measured with $F=F_{test}$). It is immediately clear that the distance z varies with the localization in the hairpin molecule of the sequence to which the sequence of the single-stranded nucleic acid is complementary. If the said single-stranded nucleic acid hybridizes with a sequence which is located close to the free ends of the hairpin, the self-rehybridization process is blocked just before the complete hairpin is reformed; in this case, $z_{pause}$ is minimal. On the other hand, if the said single-stranded nucleic acid hybridizes with a part of the hairpin which is close to the unpaired loop, the renaturation process will be arrested in a situation where the hairpin is completely, or almost completely denatured; in this case, $z_{pause}$ is maximal (FIG. 1).

It is possible to correlate precisely a physical distance in a double-stranded nucleic acid molecule with a number of bases. For example, a distance of 1 nm corresponds to the distance spanned by two nucleotides (1 bp) in a nucleic acid under a 10 pN force. The exact calibration versus force is given by the elasticity of single stranded nucleic acid. Therefore, by simply measuring the distance between the two free ends of the double-stranded nucleic acid molecule, it is possible to determine precisely where the renaturation is blocked.

Thus, in one embodiment, the invention consists of a method for determining the sequence of a nucleic acid, wherein the double-stranded nucleic acid molecule corresponding to the sequence to be determined is first denatured by application of a physical force, then rehybridized in a presence of a single-stranded nucleic acid, and the presence of a blockage in the rehybridization detected. In one aspect, the distance between the two ends of the double-stranded molecule is determined when the renaturation process is blocked. Preferentially, the distance between the two ends of the said molecule is determined when the molecule is completely denatured. Even more preferentially, the two distances are compared and the position of the blockage is determined.

Another useful parameter associated with the blockage in renaturation is the period of time during which the renaturation is blocked (referred herein as the duration of the pause in renaturation). Indeed, it is possible to measure the period of time during which the rehybridization is blocked. For example, the skilled person can determine the period of time during which the distance between the two ends of the double-stranded nucleic acid is z as defined above, i.e. an intermediate value comprised between $z_{high}$ and $z_{low}$. The duration of the blockage is dependent upon the degree of complementarity between the two sequences. The higher the complementarity, the greater the number of bonds established between the two molecules, and therefore the longer the duration. It is also clear that the blockage time will be dependent upon the length of the region of complementarity between the two sequences. The longer the region, the greater the number of bonds established between the two molecules, and therefore the longer the duration. It is therefore easily conceivable that under certain conditions the duration of the renaturation pause will be almost permanent. In particular, when the single-stranded nucleic acid comprises more than 20, preferably more than 25, even more preferably more than 30 nucleotides capable of hybridizing with the denatured double-stranded nucleic acid, the single-stranded nucleic acid remains hybridized to the double-stranded hairpin (for many minutes) even when the force applied to the said double-stranded nucleic acid is decreased to $F_{test}$, thus preventing self-rehybridization of the said double-stranded hairpin. In such a case, it may be advantageous to use an enzyme to eject the single-stranded nucleic acid molecule. The ejection of the said single-stranded nucleic acid molecule thus makes it possible to perform cycles of pairing and unpairing and thus improve the signal/noise ratio. As examples of suitable enzymes, one may cite e.g. helicases, including a UvrD helicase, E. coli UvrD helicase, Tte-UvrD helicase, T7 Gp4 helicase, RecBCD helicase, DnaB helicase, MCM helicase, Rep helicase, RecQ helicase, PcrA helicase, T4 UvsW helicase, SV40 large T antigen helicase, Herpes virus helicase, yeast Sgs1 helicase, DEAH_ATP-dependent helicases and Papillomavirus helicase E1 protein and homologs thereof. Preferably, the T4 UvsW helicase is used. The duration of the pause may also vary with the conditions of the reaction. Said duration will decrease as the temperature increases. Likewise, the buffer conditions can also modulate the duration of the pause: for example, magnesium, betain and tetramethylammonium chloride (TMAC used at molar concentration) increase the blocking time. These compounds reinforce AT pairs more than GC, thus reducing the difference in strength between these pairs. However, when the temperature and the buffer are fixed, the duration of the pause will only depend on the force pulling on the denatured double-stranded nucleic acid and on its complementarity with the single-stranded nucleic acid.

Thus, in one particular aspect, the method of the invention comprises the steps of:
    denaturing the said double-stranded nucleic acid molecule corresponding to the said nucleic acid sequence by applying a physical force to the said molecule;
    providing a single-stranded nucleic acid molecule,
    renaturing the double-stranded nucleic acid molecule in the presence of the said single-stranded nucleic acid molecule; and
    detecting a blockage of the renaturation of the said double-stranded nucleic acid molecule, and
    determining the duration of the pause.

In a preferred aspect, the detection of the blockage of the renaturation of the said double-stranded nucleic acid molecule involves determining the position of the blockage on the double-stranded nucleic acid molecule, as described above.

In this particular embodiment, the method according to the present invention may be used for diagnostic purposes to permit, in particular, the sequencing of variable regions of nucleic acid corresponding to abnormalities being looked for; the technique is then similar to the one described herebelow for sequencing.

However, it is possible to provide for a simplified technique, based on the observation that a mismatch between the oligo-nucleotide and the DNA sequence results in a much shorter lived hybridization. In a first aspect, the renaturation of a hairpin double-stranded nucleic acid molecule is blocked by a single-stranded nucleic acid, by any of the methods described above, and the duration of the blockage is determined. In a preferred aspect, this value is compared to a reference value. In a further preferred aspect, the reference value corresponds to the length of the pause observed with a reference single-stranded nucleic acid, as determined by any of the above methods.

For diagnostic purposes, e.g. looking for mutations in genomic DNA, the technique can be implemented in two ways:
  1) The hairpins formed with the genomic DNA comprising the sought for mutations are probed with oligo-nucleotides in solution.
  2) The hairpin containing the sequence(s) with the sought-for mutations are probed by the genomic DNA which is present in solution as single-stranded DNA fragments of fixed size. It will be immediately apparent that if the goal of the assay is only to find the existence of a specific sequence or possible mutation in such a sequence, placing this sequence in the loop of the hairpin provides a very simple detection scheme. If the oligo hybridizes in the loop, it completely prevents the refolding of the hairpin leading to a very large extension change, which can thus be easily detected, as described below.

The method of the invention may also be used for direct sequencing of an unknown nucleic acid. The method of sequencing of the invention affords several embodiments. In a first embodiment, a physical sequencing is achieved with the method of the invention. By successively hybridizing different known single-stranded nucleic acid probes to a nucleic acid hairpin (undergoing cycles of denaturation and renaturation), one can deduce the sequence of the said nucleic acid hairpin from the location of the pauses (measured with nm precision) during the renaturation phase.

Rather than hybridizing the double-stranded nucleic acid to be sequenced with a set of single-stranded nucleic acids representing all possible combinations of sequence, the skilled person would advantageously adopt a strategy that minimizes the number of different single-stranded nucleic acid probes. Various options are available, depending on whether the single-stranded probes, the double-stranded target molecule, or both are optimized.

In one aspect, the invention is performed with a series of single-stranded nucleic acid probes wherein only a limited number of bases are specific and the remaining are not. For example, this series of probes may consist of single-stranded nucleic acid molecules of n bases, wherein all possible di-nucleotides (e.g; AA, AT, AG, . . . , for a total of 16 possible combinations) or all possible tri-nucleotides (e.g. AAA, AAT, AAG, . . . , for a total of 64 possible combinations) are linked with all possible combinations of n-2 or n-3 nucleotides, respectively, n being an integer preferably less than or equal to 30, more preferably n is less than or equal to 20, even more preferably n is less than or equal to 8. When only 2 or 3 bases are specific (i.e. a series of 16 or 64 different probes), the position of di- or tri-nucleotides is determined at each hybridization. This allows mixing a series of single-stranded nucleic acid molecules to reduce the number of buffer exchanges. For instance, in the case of AANNNNNN, only four batches of probes are strictly necessary as implemented in the Solid sequencing platform developed by Applied Biosystems. The di- or tri-nucleotides may be located at any positions of the n-mer probes. In a preferred embodiment, the tested nucleotides are located at the center of the oligos; since this location is more sensitive to mismatch, the sensitivity of the method will be increased.

One clear advantage of the method of the invention is that said method allows for the sequencing of both strands of the double-stranded molecule at the same time. Indeed, each probe will hybridize to the strand comprising a sequence complementary to the sequence carried by the probe. The position of the hybridized probe is then determined by the unzipping/zipping method described above. Thus the sequence of both strands can be determined in the same run, providing an internal control. In order to be able to identify the strand which is bound by the probe, it is convenient to design the probe such that the di- or tri-nucleotides are located close to the center of the probes, but are slightly off-center. Another preferred embodiment of the method relates to probes wherein these nucleotides are slightly off-center, so that the blocking will be shifted depending on which strand the oligo binds to. For example, a di-nucleotide may be located immediately 5' or 3' to the center of the probe. It is also possible to use a probe where the central nucleotide is the most 5' or the most 3' nucleotide of a tri-nucleotide. For example, possible choices for an 8-mer oligo are NNXXNNNN or NNXXXNNN. Finally is it also possible to use generic bases (Z) instead of a combination of all nucleotides (N). A generic base (Z, such as 5-Nitroindole or 3-Nitropyrole) presents homogeneous interactions with all four bases and reduces dilution of the oligonucleotide.

The resolution of sequencing by mechanical detection of hybridization is limited by the achievable spatial resolution in the measurement of the distance between the bead and the anchoring surface. That resolution is ultimately determined by the rigidity of the tethering molecule (which sets the amplitude of the Brownian motion of the bead). For a molecule of about 1000 bp under a tension of about 10 pN, the spatial resolution (with one second averaging) is about 2 nm (i.e. about 2 bp (unzipped)). Since the Brownian noise decreases as the square of the DNA length (i.e. the square of the number of nucleotides), the technique is well suited to the sequencing of shorter molecules.

In another aspect, the nucleic acid to be sequenced is redesigned in order to enhance the determination of the position of the hybridizing probe. U.S. Pat. No. 6,723,513, for example, discloses a sequencing technique involving the magnification of one or more bases to aid position identification. In this technique, base pairs in the target nucleic acid are associated with four different tags (the magnifying tags) which represent each of the four bases Adenine, Cytosine, Guanine and Thymine (or Uracile, if the nucleic acid is an RNA). Every occurrence of each specific base, Adenine, Cytosine, Guanine and Thymine, is then replaced by the corresponding magnifying tag. In a preferred embodiment, each magnifying tag is an oligonucleotide of specific length, e.g. n bases, and specific sequence. The original double-stranded nucleic acid can thus be determined by unzipping/rezipping according to the method described above in the successive presence of oligonucleotides complementary to the magnifying tags for Adenine, Cytosine, Guanine and Thymine. These oligonucleotides will pair with the corresponding strand of the double-stranded nucleic acid and block its rehybridization at the corresponding coded bases.

Thus, in this aspect, the invention provides a method for the determination of the sequence as described above, wherein the single-stranded nucleic acid is an oligonucleotide complementary to one of the magnifying tags. In a preferred aspect, the method comprises a further step of determining each position of blockage for the said single-stranded nucleic acid on the double-stranded nucleic acid molecule. In a further preferred aspect, all the steps of the said method for the determination of the sequence, as well as the step of determining each position of blockage, are repeated successively with each of the oligonucleotides complementary to the magnifying tags.

Because each base is magnified, i.e. is replaced by an n-mer oligonucleotide, the accuracy required for determining the position of the hybridizing probe needs only be inferior to n nm. For example, if the magnifying tag is an 8-mer oligonucleotide, the position of the base can be determined accurately when it is possible to determine a physical distance between the two free ends of the molecule with a precision of less than 8 bases, i.e. less than 8 nm. Another advantage of this approach is that many beads can be sequenced in parallel with only four successive assays.

In a second embodiment, the method of the invention comprises an enzymatic step. One preferred embodiment of this approach consists in sequencing the hairpin by the successive hybridization and ligation of complementary sequences. It is possible, in this embodiment of the method of the invention, to determine the sequence of long double-stranded nucleic acid molecules; by long double stranded nucleic acid molecules, it is herein understood molecules of more than 500 bp, more preferably of more than 750 bp, even more preferably of more than 1000 bp. The technique consists in ligating to an upstream single-stranded nucleic acid primer an adjacent hybridized single-stranded nucleic acid. The extension of the primer is then monitored by denaturing and renaturing the hairpin double-stranded nucleic acid molecule and detecting a blockage in renaturation, as described above. The method is then repeated with a different single-stranded nucleic acid molecule. According to the method of the invention, no preliminary amplification of the double-stranded nucleic acid molecule to be sequenced is required; the method of the invention can be performed on a single double-stranded nucleic acid molecule.

In a preferred embodiment, a library of single-stranded nucleic acid molecules is used (see e.g. U.S. Pat. Nos. 4,882,127 and 4,849,077). Said library consists of single-stranded nucleic acid molecules of n bases, wherein all possible di-nucleotides (e.g. AA, AT, AG, ..., for a total of 16 combinations) are linked at their 3' end by all possible combinations of n-2 nucleotides, n being an integer preferably less than or equal to 20, more preferably n is less than or equal to 12, even more preferably n is less than or equal to 8. In a more preferred embodiment, the last m nucleotides are cleaved before performing the next round of hybridization and ligation, m being an integer comprised between 1 and n-1; preferably, m is equal to n-1 (Mir et al., *Nucleic Acids Res.*, 37(1): e5, 2009). The use of a cleavable sequence allows for detection of hybridization with less stringent requirement on the accuracy of the blockage position (a few nm) while still keeping a low number of synthesis steps. An alternative is to use oligos missing a phosphate on their 5' end so that only one oligo can be ligated at a time; before the next run a kinase is used to add the missing phosphate thereby allowing the next ligation. By repeating this procedure with each of the 16 possible di-nucleotides, it is possible to detect the successive increase in length of the complementary strand upon ligation of each of the successive single-stranded oligo-nucleotides. It is also possible to pool the 16 oligonucleotides in 4 batches to reduce the number of assays. Since each dinucleotide sequence is detected twice this is sufficient to determine the sequence. Once the whole double-stranded nucleic acid has thus been complemented by the library of single-stranded nucleic acid molecules, the synthesized strand is ejected (for example with the help of a helicase, or an exonuclease) and the process is reinitiated with an upstream single-stranded nucleic acid primer which is shifted upstream or downstream by one nucleotide with respect to the previous primer. Repeating the procedure n-m times allows for the complete determination of the double-stranded nucleic acid sequence: for example, for a library of 8-mer oligomers, only 5 repeats of the procedure (i.e. synthesis of a complementary strand) are needed to obtain the complete sequence of the double-stranded molecule when m=3.

Whereas the methods of the prior art all use fluorescent nucleotides, the method of the invention only involves the mechanical detection of the probe's extension. Therefore the method of the invention does not suffer from any of the drawbacks associated with the methods of the prior art. For example, the successful ligation of an 8-mer oligomer represents a change in extension of the double-stranded hairpin of 8 nm. This can easily be detected with a resolution of 2 nm, which is the spatial resolution (with one second averaging) for a molecule of about 1000 bp under a tension of about 10 pN. Since at each step a single oligonucleotide is ligated, its detection implies only the detection of a relative change in extension, i.e. before and after successful ligation.

Implementation of the method of the invention has been made possible, in particular, by the existence of devices designed for probing real-time nucleic acid interaction at the single-molecule level. Such a device is described for example in U.S. Pat. Nos. 7,052,650 and 7,244,391. The apparatus described therein uses magnetic traps to apply a picoNewton scale force on a micron-sized superparamagnetic bead. Briefly, the said apparatus comprises an optical microscope, magnets and a PC. The double-stranded nucleic acid molecules are anchored at multiple points at one end to a motionless element, e.g. a surface, and at the other end to a movable surface, in this case a magnetic bead. Magnets are provided for acting on the bead. In particular, the magnets may be used for pulling the bead away from the surface. However, the implementation of the method of the invention is not restricted to the above apparatus. Any device which allows one to fully extend and then refold a molecule of double stranded nucleic acid, whilst monitoring at the same time the extension of the said molecule can be used to implement the method of the invention. For example, optical tweezers may be used; they require however prior force calibration and are not easily parallelized for high throughput measurements. Further drawbacks are the lack of total torsional control of the nucleic acid and the possible local heating of the solution by the focussed laser which may alter the hybridization conditions.

The double stranded nucleic acid is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation.

The bead-nucleic acid assembly is injected in a fluidic chamber the surface of which has been treated such as to bind the other labeled end of the molecule (for example a surface coated with anti-Dig to bind the Dig-labeled end of the nucleic acid). The beads are thus anchored to the surface via a nucleic acid hairpin, see FIG. 1. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the nucleic acid molecule anchoring the beads to the surface various techniques have been described. One can use the light of a focused laser beam to trap a transparent bead near the focal point. By the relative translation of the beam with respect to the anchoring surface one can apply a force on the tethering molecule (a typical optical tweezers assay). The exerted force being proportional to the displacement of the bead from its equilibrium position, to exert a constant force on the tethering molecule requires a feedback loop on the trapping beam.

To exert a constant force on a bead, the use of the hydrodynamic drag generated by a flow around the bead has been described, but it usually yields a low spatial accuracy (>100 nm). The preferred embodiment uses a magnetic trap to pull on superparamagnetic beads anchored to a surface by a nucleic acid hairpin as described above.

In this configuration, small magnets placed above the sample are used to apply a constant force on the anchored bead, whose position can be determined with <1 nm accuracy (depending on the pulling force and the dissipation due to hydrodynamic drag) In every case one notices that the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, some molecules in solution (such as proteins or complementary oligonucleotides of DNA, RNA, LNA or PNA) have bound to the stretched single stranded nucleic acid, these molecules will block the rezipping of the hairpin when the force is lowered to below 11 pN. The principle of the assay is thus to switch between two forces: a large one $F_{open}$ to open the hairpin and a smaller one $F_{test}$ used to allow re-zipping and to measure the extension of the molecule at transient blockages. The blocking position is related to the sequence by a linear relation between full extension and the blocked one. For best accuracy, the full extension is preferably measured at the test force $F_{test}$. This is achieved by designing the hairpin loop such that it requires a fraction of a second to refold once the force is reduced from $F_{open}$ to $F_{test}$.

In order to attach nucleic acids to surfaces or supports, use may be made of any one of the techniques known in the field. Essentially, the nucleic acid becomes anchored directly to the support, for example the micro-bead, which involves a functionalization of this surface, for example by coating it with streptavidin, a COOH group, and the like, capable of reacting with the functionalized end of the nucleic acid.

Such methods necessitate, in general, functionalizing the nucleic acid, especially the 3' and 5' ends, that is to say grafting appropriate chemical groups onto them. It is, moreover, preferable to join the other two free ends of the molecule by a loop in order to prevent the strands from dissociating at the end of the operation, so that the latter can be repeated if appropriate. For this purpose, different procedures may be adopted. The simplest is to functionalize, using synthetic oligonucleotides, one of the ends of a double-stranded nucleic acid with two different functions (biotin and amine, for example), which permit anchoring to two different pre-treated surfaces. The two strands at the other end may be joined using a partially paired synthetic nucleotide in the form of a loop. In this way, a paired, single-stranded nucleic acid, i.e. a hairpin, is produced from a double-stranded nucleic acid. The advantage of this method lies in its capacity to functionalize a heterogeneous population of large nucleic acid fragments (as are obtained by fractionation of a gene or chromosome), which can then be analyzed simultaneously. In this case, the nucleic acid sample is fractionated using two (or more) restriction enzymes, which enables a subpopulation to be obtained with two different restriction sites at its ends which are similar over all the fragments. This enables the two ends to be treated differently (for example by joining one end to an oligonucleotide in the form of a loop possessing the appropriate restriction site at its end). The drawback of this method lies in the steric interference between the two adjacent functional groups, which can make coupling to the surfaces difficult. To solve this problem, it can be advantageous to add at each free end of the hairpin molecule a "spacer" sequence of bases, to the end of which a functional group is then added; the two spacer sequences are non-complementary, affording each functional group enough space to bind to its dedicated surface. More advantageously, the sequence of each spacer sequence is designed in order to use single-stranded sequencing primers of known sequence in the sequencing method of the invention. The addition of a loop and/or spacers to the double-stranded nucleic acid molecules can be performed with any of the methods commonly used in molecular biology. These methods are well known to the person skilled in the art and there is thus no need to detail them here.

As regards the actual anchoring techniques, there are many of these and they derive from the techniques for anchoring macromolecules (proteins, DNA, and the like) to commercially available pretreated surfaces. Most of these techniques have been developed for immunology tests, and link proteins (immunoglobulins) to surfaces carrying groups (—COOH, —NH$_2$, —OH, and the like) capable of reacting with the carboxyl (—COOH) or amine (—NH$_2$) ends of proteins.

The covalent anchoring of nucleic acid may be accomplished directly, via the free phosphate of the 5' end of the molecule, which reacts with a secondary amine (Covalink —NH surface marketed by Polylabo at Strasbourg) to form a covalent bond. It is also possible to functionalize DNA with an amine group and then to proceed as with a protein.

There are also surfaces coated with streptavidin (Dynal beads, and the like), which permit quasi-covalent anchoring between the streptavidin and a biotinylated DNA molecule. Lastly, by grafting an antibody directed against digoxigenin onto a surface (by the methods mentioned above), a nucleic acid functionalized with digoxigenin may be anchored thereto. This represents merely a sample of the many possible anchoring techniques.

Among the attachment and anchoring techniques, there should also be mentioned, for example, the techniques described in Patent EP 152 886 using an enzymatic coupling for the attachment of DNA to a solid support such as cellulose.

Patent EP 146 815 also describes various methods of attachment of DNA to a support. Similarly, patent application WO 92/16659 proposes a method using a polymer to attach DNA.

Naturally, the nucleic acid may be attached directly to the support but, where necessary, especially with a view to limiting the influence of the surfaces, the nucleic acid may be attached at the end of an inert arm of peptide or other nature, as is, for example, described in Patent EP 329 198.

The examples below will enable other features and advantages of the present invention to be brought out.

LEGENDS OF THE FIGURES

FIG. 1 Principle of detection of the hybridization of oligo-nucleotides to their complementary sequence on a hairpin DNA. The hairpin DNA anchoring the bead to the surface (a) is momentarily unzipped by increasing the force pulling on the bead to a value above 16 pN. In that phase the complementary fragment in solution hybridizes to its target on the opened DNA hairpin, thus preventing the rezipping of the hairpin (b) when the force is reduced back to its initial value. The hairpin refolding presents four plateaus occurring at well defined extensions but with variable duration. The top plateau at 73.71 nm is associated with the 83 bp fully opened hairpin at $F_{test}$, while the bottom one corresponds to the hairpin completely refolded. The two intermediate plateaus at 25.47 nm and 35.17 nm occur because two oligos have been placed in the solution. From these change in extension ($z_{high}$-z) it is possible to deduce where along the hairpin the complementary sequence has paired. Here according to their positions the blocks coincide with location 28.66 bp and 39.60 bp in very good agreement with their expected positions at 29 bp and 40 bp. The plateau positions are better estimated by fitting Gaussian to the histogram obtained from several opening/closing cycles (here ~20 cycles).

Figure 2:
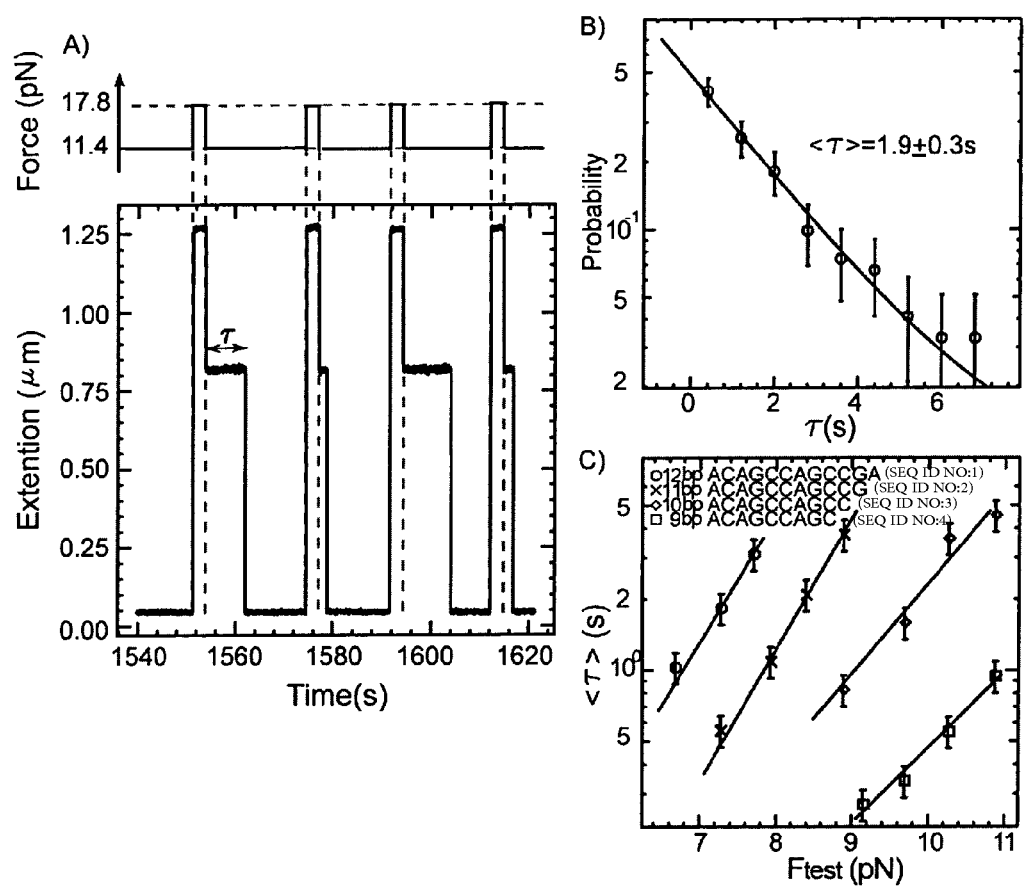

FIG. 2 The blocking time strongly depends on the oligo-nucleotide length and on the pulling force. FIG. 2A) Blockages of time a due to a 10 bases oligo-nucleotide on a 1200 bp hairpin. FIG. 2B) Histogram of the blocking time displays a Poisson distribution with a 2 seconds mean value. FIG. 2C) The blocking time varies with the oligo-nucleotide size (SEQ ID NOs. 1-4) and varies exponentially with the force $F_{test}$ used during the test phase.

Figure 3:
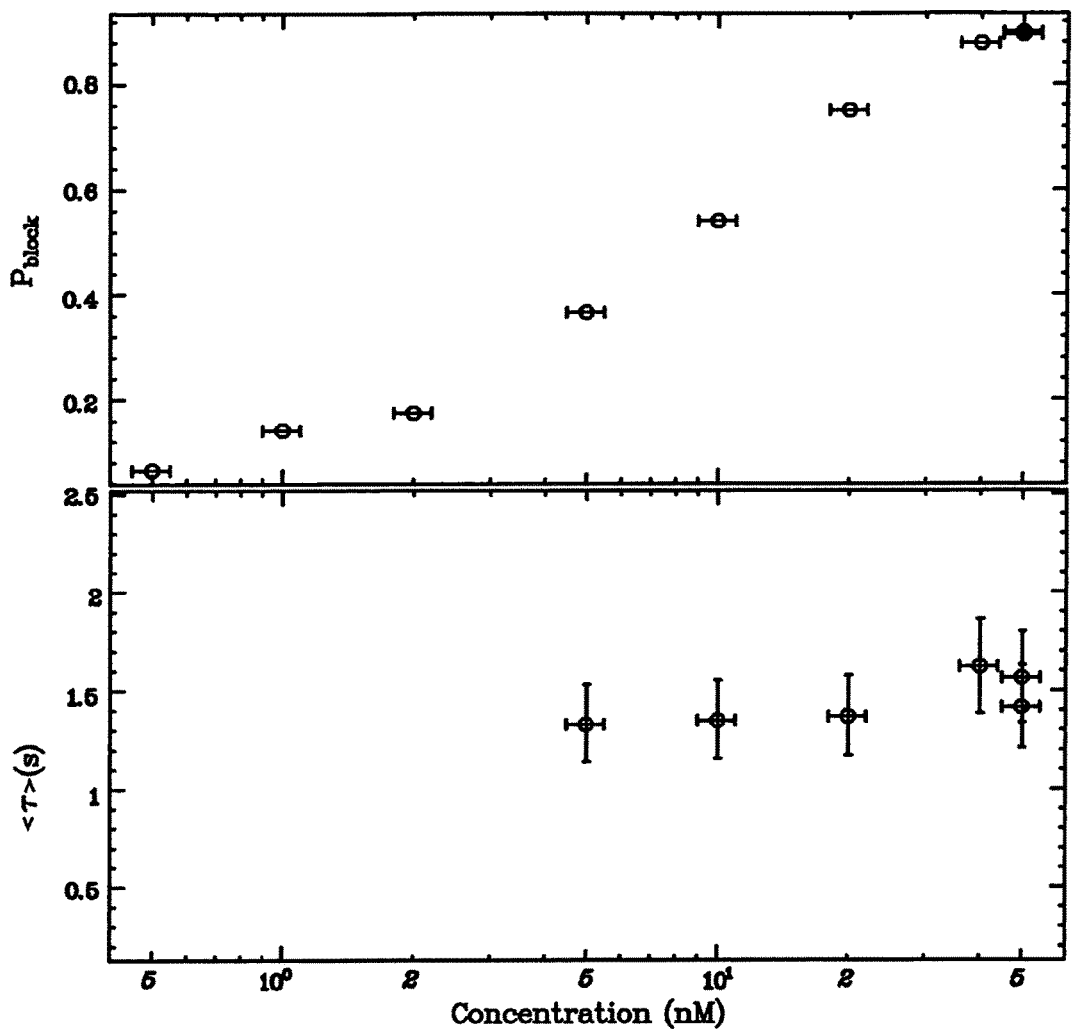

FIG. 3 Evolution of the blocking probability and blocking time with the oligo concentration in the case of a 9 bases oligo. The blocking time is independent of the concentration. The blocking probability presents a Km of 10 nM FIG. 4 The blocking time of oligonucleotides having 12 nucleotides (Target: SEQ ID NO: 5; Probes: SEQ ID NOs: 6-11) are plotted versus force. Except the curve with circular symbols, all these oligonucleotides have one or two mismatches, though in that later case the blockage was too short to be measured. If the mismatch is located on the last or first base, the blocking time is reduced by a factor five. If the mismatch concerns an AT base pair in the middle of the oligonucleotide the blocking time is reduced by more than 20 times, whereas it reaches 60 times if it concerns a GC base pair. A double mismatch reduces the blocking time so much that it cannot be measured.

Figure 5A:
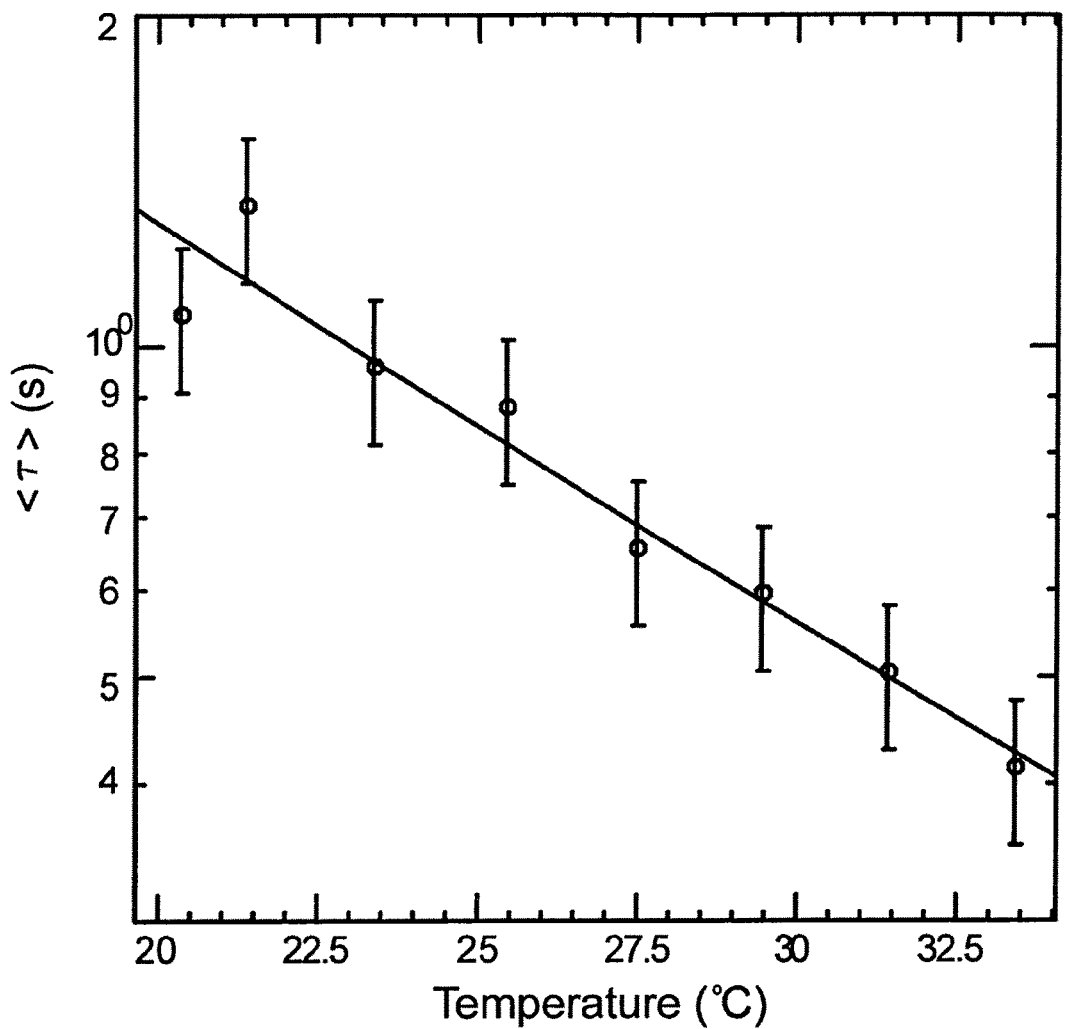

FIG. 5a Evolution of the blocking time with temperature for 10 oligonucleotides ACAGCCAGCC. Typically the blocking time decreases by a factor 3 when temperature increases by 10 degrees.

Figure 5B:
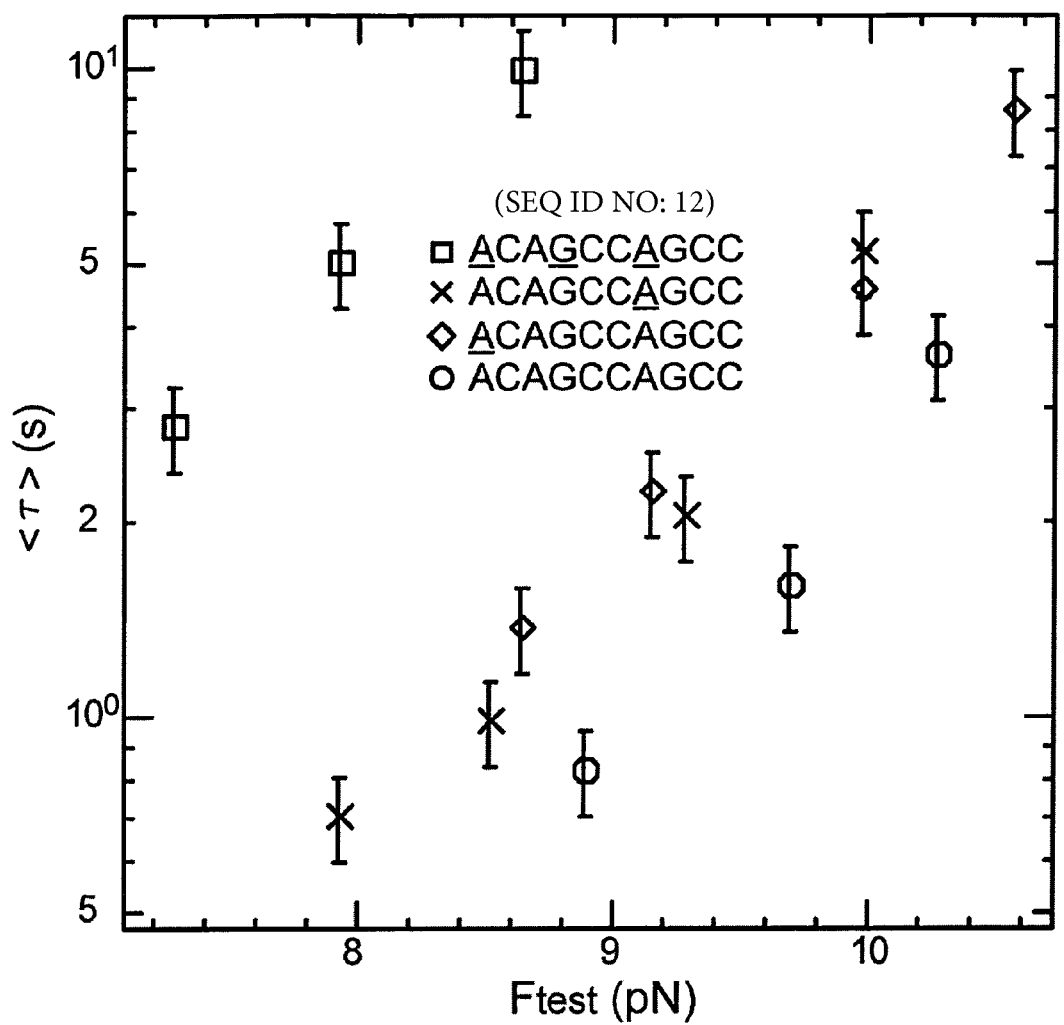

FIG. 5b The blocking time of oligonucleotides having 10 bp nucleotides (SEQ ID NO: 12) are plotted versus force. Except the curve with circular symbols, all the oligonucleotides have one or three LNA (marked with square symbols). One LNA replacing DNA increases the blocking time by more than 2 times.

Figure 6:
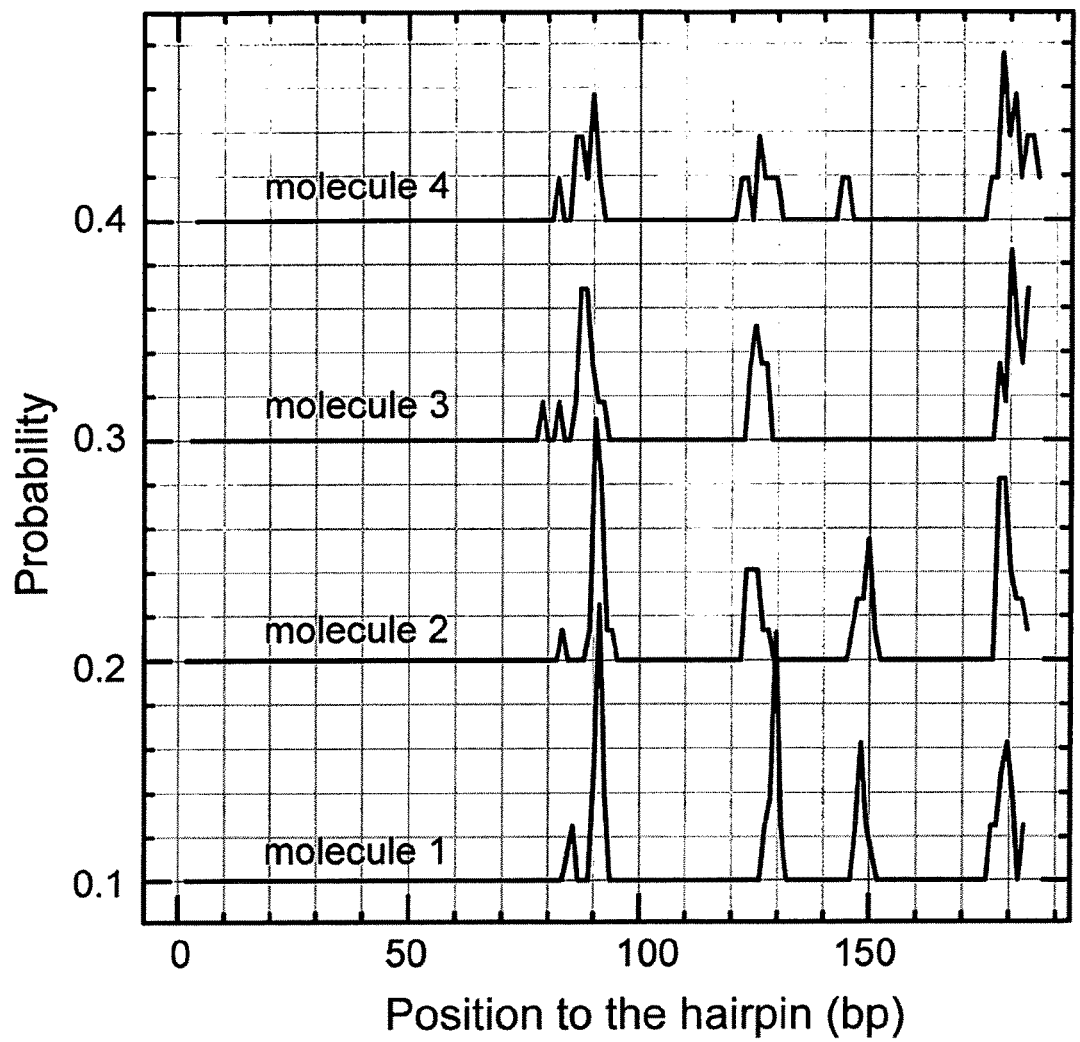

FIG. 6: Histogram of the distribution of DNA extensions in an experiment such as the one displayed in FIG. 1c, where oligo-nucleotides in solution can pair with the unzipped DNA at various positions along the molecule. From the position of the histogram peaks (which is highly correlated for three different molecules, i.e. different bound beads) the position of the hybrid along the DNA can be deduced.

Figure 7:
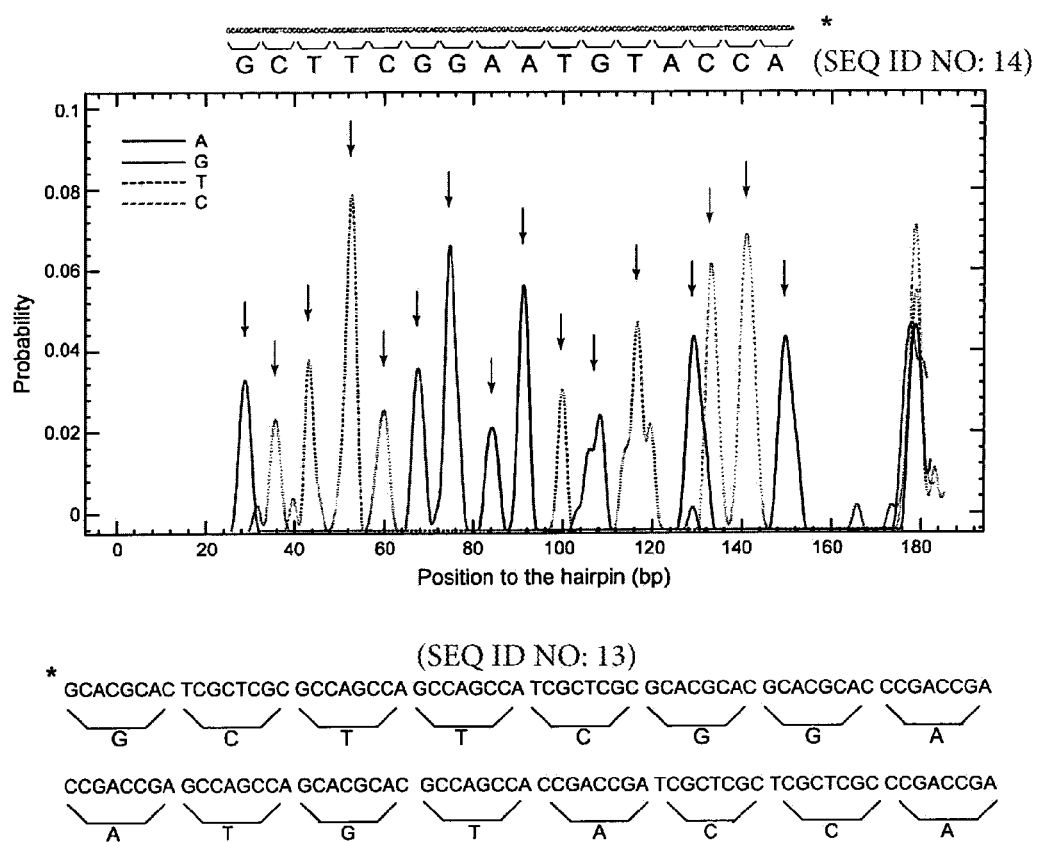

FIG. 7: Histograms of blocking positions (SEQ ID NO: 14) corresponding to the four 8 bases nucleotides $A_8$, $C_8$, $T_8$, $G_8$ for a DNA hairpin corresponding to a magnified sequence (SEQ ID NO: 13). These blocking positions correspond precisely to their expected positions. We have here $G_8$=GCACGCAC, $C_8$=TCGCTCGC, $T_8$=GCCAGCCA and $A_8$=CCGACCGA.

EXPERIMENTAL EXAMPLES

DNA Preparation

A double-strand (ds) DNA fragment of unknown sequence and of a size comprised between a few tens and a few thousands base-pairs, is ligated at one of its extremities to a DNA loop. Its other extremity is ligated to a dsDNA fragment allowing for the binding of its two strands to differently coated surfaces. For example the free 3' end of one strand can be labeled with biotin allowing binding to streptavidin coated beads, whereas the 5' end on the opposite strand can be labelled with digoxigenin allowing its binding to surfaces coated with an anti-Dig antibody. This end-labelling can be done by various ways known to the man of the art, such as the use of terminal transferase to add biotin (or dig) modified nucleotides or hybridization with suitably labeled oligo-nucleotides.

Force Stretching Apparatus

This DNA construct is incubated for a few minutes in a solution of adequate beads (for example streptavidin coated ones) to which it binds by one of its labeled (for example biotin) ends. The beads can be transparent if optical tweezers are later used for manipulation or magnetic if one uses magnetic traps or tweezers for manipulation. The bead-DNA assembly is injected in a fluidic chamber the surface of which has been treated such as to bind the other labeled end of the molecule (for example a surface coated with anti-Dig to bind the Dig-labeled end of the DNA). The beads are thus anchored to the surface via a DNA-hairpin, see FIG. 1a. The distance of the bead to the surface is then monitored by various means known to the man of the art: for example the diffraction rings of their image on a camera can be used to deduce their distance, or the light intensity they scatter (or emit by fluorescence) when illuminated in an evanescent mode can be used to measure their distance. Alternatively, the magnetic field they generate can be measured (using a magnetic sensor such as GMR or Hall sensors) to deduce their distance to a sensor on the anchoring surface.

To pull on the DNA molecule anchoring the beads to the surface various techniques have been described. The preferred embodiment uses a magnetic trap to pull on superparamagnetic beads anchored to a surface by a DNA hairpin as described above. In this configuration, small magnets placed above the sample are used to apply a constant force on the anchored bead, whose position can be determined with <1 nm accuracy (depending on the pulling force and the dissipation due to hydrodynamic drag). In this series of experiments, the apparatus described in U.S. Pat. Nos. 7,052,650 and 7,244,391 was used. In addition, unless otherwise indicated, the experiments reported her were performed in 25 mM Tris pH 7.5, 150 mM KAc, 10 mM $MgCl_2$, 0.2% BSA. In every case, the tethering hairpin can be mechanically fully unzipped by pulling on the beads with a force larger than about 16 pN. Reducing the tension on the molecule to below about 11 pN allows the hairpin to re-zip spontaneously (the unzipping transition is reversible though hysteretic). If, during the unzipped phase, some molecules in solution (such as proteins or complementary oligo-nucleotides of DNA, RNA, LNA or PNA) have bound to the stretched single stranded (ss)DNA, these molecules will transiently block the rezipping of the hairpin when the force is lowered to below 11 pN. The principle of the assay is to switch between two forces: a large one $F_{open}$ to open the hairpin and a smaller one $F_{test}$ used to allow re-zipping and to measure the extension of the molecule at transient blockages. The blocking position is related to the sequence by a linear relation between full extension and the blocked one. For best accuracy, the full extension is preferably measured at the test force $F_{test}$. This is achieved by designing the hairpin loop such that it requires a fraction of a second to refold once the force is reduced from $F_{open}$ to $F_{test}$.

The Hybridization Position of an Oligo-Nucleotide can be Measured with a Basepair Resolution By measuring the extension of the DNA molecule (the distance of the bead to the surface) during one of these rezipping pauses, it is possible to determine the position of the blockage with a nanometer precision (1 nm corresponds to the distance spanned by two nucleotides (1 bp) in a ssDNA under a 10 pN force). The unzipping configuration displays the largest ratio of extension to basepair (in dsDNA the ratio is only 0.34 nm per bp).

The accuracy of this measurement is limited by two noise contributions:

The accuracy of the measuring method,

The brownian motion of the bead.

Different techniques can be used to measure the vertical position of the bead. One of the simplest relies on video microscopy (U.S. Pat. Nos. 7,052,650 and 7,244,391). The results in FIG. 1 where obtained with this method, typical resolution reaches 1 nm for a 1 second averaging. Other methods with better resolution have been demonstrated, such as laser illumination with PSD sensors that reaches 0.1 nm in resolution (Greenleaf and Block, *Science,* 313: 801, 2006) and evanescent wave illumination (Singh-Zocchi et al., *Proc Natl Acad Sci USA.,* 100(13): 7605-7610, 2003, Liu et al., *Biophys J.,* 96(9): 3810-3821, 2009).

The intrinsic limitation in resolution is given by the brownian fluctuations of the bead pulling on a ssDNA molecule. $<x^2>=4k_BT \Delta f (6\pi\eta r)/k^2_{ssDNA}(F)$ where $k_{ssDNA}(F)$ is the stiffness of a ssDNA molecule, $k_B$ is Boltzman constant, T the absolute temperature, $\eta$ the viscosity of water, r the bead's radius and $\Delta f$ is the frequency range of the measurement. $k_{ssDNA}(F=10\ pN)=0.05/Nb$ (N/m), where Nb is the number of bases of the ssDNA. For the 84 bp hairpin this leads to 0.04 nm of noise over 1 second ($\Delta f=1$ Hz) averaging. The larger noise in FIG. 1 ($\sigma \sim 1$ nm) is essentially due to the measuring device, not the intrinsic fluctuations. The intrinsic brownian noise increases with the size of the hairpin: a 1200 bp hairpin leads to a noise of 0.6 nm when averaging over 1 second.

The Quality of Hybridization is Measured by the Mean Value of the Blocking Time.

The blocking strength can be characterized by two parameters: the probability of blocking $P_{block}$ (=the number of cycles presenting a blockage/the total number of cycles) and the mean time of blocking $\tau_{block}$. $P_{block}$ depends on $k_{on}$, and the oligonucleotide concentration while $\tau_{block}$ depends only on $k_{off}$, where $k_{on}$ and $k_{off}$ are respectively the binding and unbinding reaction constant. On FIG. 2 is displayed the typical variation of $\tau_{block}$ with the oligonucleotide length and the force. A single base mismatch has a drastic effect on $\tau_{block}$, equivalent to reducing the oligonucleotide length by at least one nucleotide and decreasing the blocking time by a factor 5.

In practice $\tau_{block}$ and thus $k_{off}$ is simpler to measure since it does not depend on the oligonucleotide concentration (FIG. 3). However it is also possible to measure $k_{on}$. The average blocking time depends on the oligonucleotide sequence but not on its position along the hairpin. A sequence matching two specific positions along the hairpin was studied: the blocking time is the same for both blockages while they occur at very different locations.

A Single Mutation has a Drastic Effect on the Blocking Time

Figure 4:
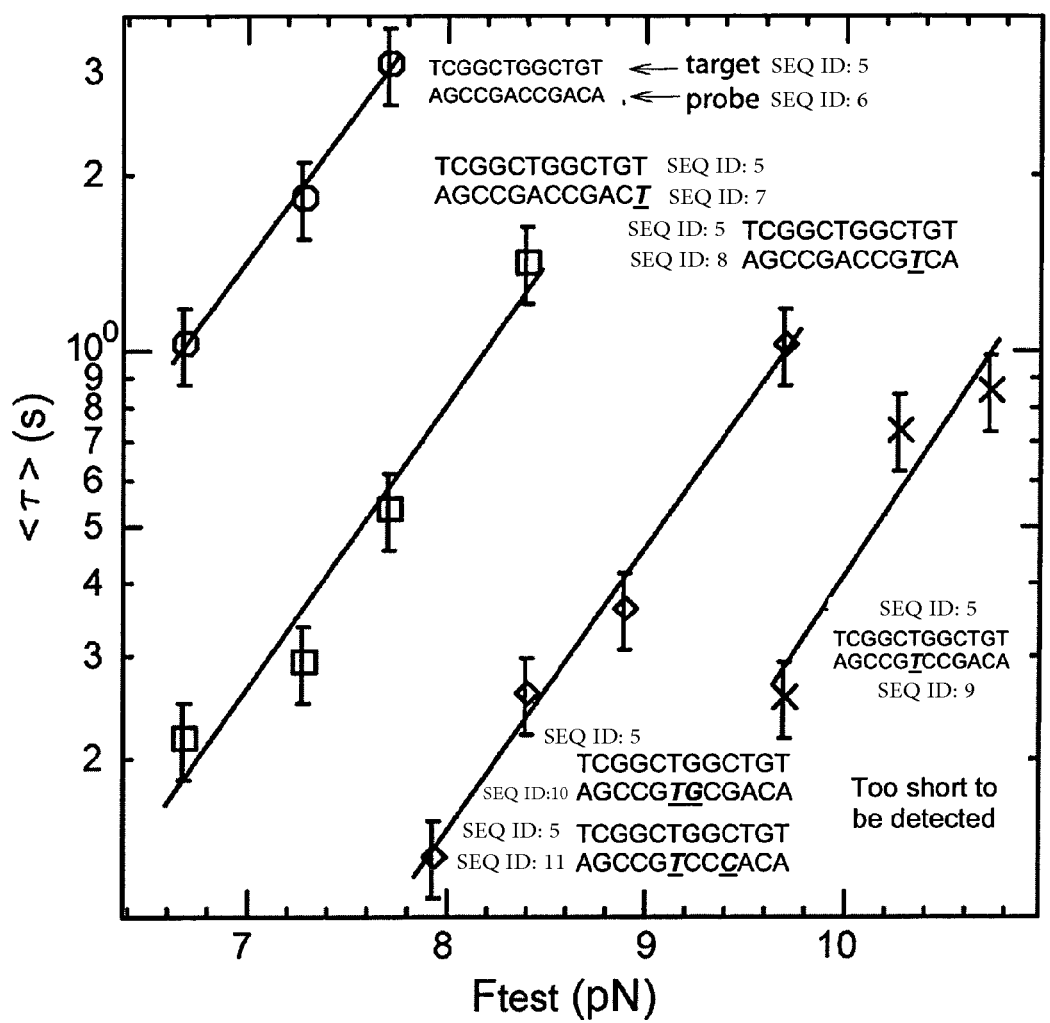

As shown on FIG. 4, an oligo of 12 bases forming a perfect match with the hairpin presents a very different blocking time than the same oligo with a single mismatch. In FIG. 4 the blocking time versus force for the different oligos is shown. Increasing the force increases the blocking time. When the mutation is just at the first or last nucleotide, its effect on the blocking time is minimal reducing it by a factor five. As expected, this reduction depends on the nature of the mismatch, a mismatch on AT typically leads to a blocking time reduction of a factor 20 while a GC mismatch leads to a reduction of a factor 60.

The Blocking Time is Drastically Reduced when the Mismatch is Located in the Centre of the Oligo.

As can be seen on FIG. 4, a mismatch in the centre of the oligo-nucleotide causes a very short blockage observable only when the force is maximal. The reduction in blocking time resulting from such a mismatch exceeds a factor 100 for the same force conditions.

The Blocking Time Depends on Temperature and Buffer Conditions.

As seen on FIG. 5a, increasing the temperature significantly reduces the blocking time. The buffer conditions can also modulate the blocking time: magnesium, betain and tetramethylammonium chloride (TMAC used at molar concentration) significantly increase the blocking time by comparison to the buffer used in these experiments (25 mM Tris pH 7.5, 150 mM KAc, 10 mM $MgCl_2$, 0.2% BSA). These compounds reinforce AT pairs more than GC reducing the difference in strength between these pairs.

The Blocking Time Increases Using RNA or LNA Oligo-nucleotides.

RNA and LNA oligo-nucleotides form stronger hybrids with ssDNA than DNA oligo-nucleotides. For the same target sequence, the blocking time increases by a factor 2 for an RNA oligo-nucleotide as compared to a DNA oligo-nucleotide.

LNA nucleotides have a more drastic effect: if a single nucleotide is converted from a DNA to an LNA the blocking time of the full oligo-nucleotide is increased by a factor 2. Converting Three Bases From DNA To LNA Increases The Blocking Time By a Factor 5. Changing all nucleotides from DNA to LNA as such a drastic effect that the blocking time of a 10 bases LNA oligo-nucleotides exceeds 1 h. Reducing the size of the oligo-nucleotide to 6 bases of LNA leads to a reasonable blocking time of 1 second.

As with DNA oligo-nucleotides, by measuring the mean time of blockage with one of these alternative oligo-nucleotides (LNA or RNA) one can determine its nature: is it due to a perfect hybridization with a complementary oligo-nucleotide or not and if not where is the mismatch (for example at the center of the hybridized oligo-nucleotide or near one of its ends).

Length of Detectable Oligo-Nucleotide.

Since the blocking time depends exponentially on the oligo-nucleotide length, this parameter cannot be varied much. If the oligo-nucleotide is too small (smaller than 8 bases at room temperature) the blocking time is too small to be detectable. If the oligo is too large (greater than 12 bases at room temperature) the blocking time becomes too long.

Enzymes May Stabilize the Hybrid.

Adding gp43 DNA polymerase without NTP increase the blocking time of oligo-nucleotides. This is expected since the hybridized primer is a substrate for the polymerase. The gp43 polymerase increase the blocking time of an oligo by a factor 10.

Summary of Hybridization Parameters

The length of the oligo is a critical parameter: at room temperature the length of oligo-nucleotides with practical blocking times varies from 8 to 12 bases. One can easily perform a series of unzipping/rezipping experiment on the same molecule and measure the mean time of blockage upon rezipping due to pairing of oligo-nucleotides with the DNA in the unzipped phase. This time depends on the size of the oligo-nucleotide, the force applied during rezipping, the temperature and the ionic concentration. If the paired fragment displays mismatches the blockage time will be reduced significantly (at least 10 times) and in a quantifiable way. The mechanical unzipping/rezipping technique thus allows one to probe quickly the position and stability of pairing between a known oligo-nucleotide sequence and a DNA fragment of unknown sequence, see FIG. 1c and FIG. 2. These observations suggest various implementations for applications in DNA sequencing and diagnostics.

Diagnostics and Sequencing by Mechanical Detection of Hybridisation.

By probing the DNA hairpins anchoring the beads to the surface with different oligo-nucleotides (introduced successively in the fluidic chamber), one can either determine the presence of possible mutations on a known sequence (resulting in mismatches with the probe oligonucleotide and shorter pauses during rezipping) or sequence an unknown DNA by determining the position of known probes along the molecule, see FIG. 6.

In another aspect, the nucleic acid to be sequenced is redesigned by the use of magnifying tags in order to enhance the determination of the position of the hybridizing probe. In the experiment reported in FIG. 7, every occurrence of each specific base, Adenine, Cytosine, Guanine and Thymine, was replaced by the corresponding magnifying tag, in this case an 8-mer oligonucleotide. As shown in FIG. 7, the blocking positions correspond perfectly with the expected positions from the sequence.

The invention claimed is:

1. A method for determining a nucleic acid sequence in a double-stranded nucleic acid molecule, said method comprising:
   a) providing a sample containing said double-stranded nucleic acid molecule comprising said nucleic acid sequence; wherein:
      said double-stranded nucleic acid molecule is a hairpin,
      at least one base of a first strand of said hairpin is attached directly or indirectly to a support, and
      at least one base of a second strand of the hairpin is attached to a movable support, wherein the moveable support is a magnetic bead;
   b) completely denaturing the double-stranded nucleic acid molecule of step a) by applying a magnetic force above the sample, thereby producing a completely denatured double-stranded nucleic acid molecule, wherein said completely denatured double-stranded nucleic acid molecule is a completely extended single-stranded nucleic acid molecule;
   c) measuring the distance ($Z_{high}$) between the two ends of the completely denatured double-stranded nucleic acid molecule obtained in step b), said two ends being attached to the support and the movable support;
   d) hybridizing a single-stranded nucleic acid molecule having a known sequence with said completely denatured double-stranded nucleic acid molecule obtained in step b), thereby producing a complex;
   e) renaturing said completely denatured double stranded nucleic acid molecule of said complex in step d);
   f) detecting a blockage of the renaturation of said completely denatured double-stranded nucleic acid of said complex, wherein said blockage is caused by said single-stranded nucleic acid molecule of said complex; and
   g) determining the position of said blockage with respect to one end of the double-stranded nucleic acid molecule, the determining step comprising the steps of:
      measuring distance (z) between the two ends of the double-stranded nucleic acid molecule which are attached to the support and the movable support during the period of said blockage,
      comparing z and $Z_{high}$, and
      defining the position of the blockage; and
   h) ejecting the single-stranded nucleic acid molecule from said complex; wherein said nucleic acid sequence of said double-stranded nucleic acid molecule is determined based on the position of said blockage and the known sequence of the single-stranded nucleic acid molecule of step d).

2. The method of claim 1, wherein a magnetic force above or equal to 15 pN is applied to the double-stranded nucleic acid molecule to completely denature the double-stranded nucleic acid by moving the moveable support away from the support in step b).

3. The method of claim 2, wherein said magnetic force is above or equal to 17 pN.

4. The method of claim 1, wherein the completely denatured double-stranded nucleic acid is renatured in e) by reducing the magnetic force.

5. The method of claim 4, wherein the magnetic force applied to the completely double-stranded molecule is reduced to less than or equal to 12 pN.

6. The method of claim 5, wherein said magnetic force is reduced to less than or equal to 11 pN.

7. The method of claim 1, further comprising measuring duration of the blockage.

8. The method of claim 7, further comprising comparing the duration of the blockage with a reference value.

9. The method of claim 1, wherein the single-stranded nucleic acid molecule is selected from a library of n-mer single-stranded nucleic acid molecules, said library comprising all possible combinations of di- or tri-nucleotides linked with all possible combinations of n-2 or n-3 nucleotides, respectively, n being an integer less than 30.

10. The method of claim 9, wherein the di- or trinucleotides are located at a centre of the single-stranded nucleic acid molecule.

11. The method of claim 9, wherein the di- or trinucleotides are located off-centre of the single-strand nucleic acid molecule.

12. The method of claim 1, comprising, between steps a) and b), a further step of replacing a base selected from adenine, cytosine, guanine, and thymidine in the double-stranded nucleic acid with a specific magnifying tag, said magnifying tag being an oligonucleotide.

13. The method of claim 12, wherein the single-stranded nucleic acid of step d) is an oligonucleotide complementary to a magnifying tag.

14. The method of claim 1, wherein step d) further comprises the steps of:
   A) providing a first single-stranded nucleic acid primer $P_i$ and a second single-stranded nucleic acid primer $P_j$, wherein primer $P_i$ and primer $P_j$ are complementary to adjacent sequences of said double-stranded nucleic acid molecule of step a);
   B) hybridizing the primer $P_i$ and the primer $P_j$ with said completely denatured double-stranded nucleic acid molecule obtained in step b), thereby producing a first product; and
   C) ligating one end of the primer $P_i$ to one end of the primer $P_j$ on the first product.

15. The method of claim 14, wherein step d) further comprises the steps of:
   A) providing a ligated single-stranded nucleic acid primer comprising the primer $P_i$ and the primer $P_j$ and a third single-stranded nucleic acid primer $P_k$, wherein:
      the primer $P_k$ is different from the primer $P_i$;
      the primer $P_k$ is different from the primer $P_j$; and
      the primer $P_j$ and the primer $P_k$ are complementary to adjacent sequences of said double-stranded nucleic acid molecule of step a);
   B) hybridizing the ligated single-stranded nucleic acid primer and the primer $P_k$ with said completely denatured double-stranded nucleic acid molecule obtained in step b), thereby producing a second product; and
   C) ligating one end of the ligated single-stranded nucleic acid primer to one end of the primer $P_k$ on the second product.

16. The method of claim 14, wherein $P_j$ is selected from a library of n-mer single-stranded nucleic acid molecules, said library comprising all possible combinations of dinucleotides linked at their 3' end to all possible combinations of n-2 nucleotides, n being an integer less than 20.

17. The method of claim 14, wherein step d) further comprises the steps of:
   i) providing a third single-stranded nucleic acid primer $P_x$, and a fourth single-stranded nucleic acid primer $P_y$, wherein:
      the primer $P_x$ and the primer $P_y$ hybridize with adjacent sequences of said completely double-stranded nucleic acid molecule.

18. The method of claim 1, wherein steps a) to h) are repeated.

* * * * *